United States Patent [19]

Sachtler et al.

[11] Patent Number: 4,859,331
[45] Date of Patent: Aug. 22, 1989

[54] SYSTEM FOR EXCHANGING A SUBSTANCE BETWEEN FLUIDS

[75] Inventors: Jürgen Sachtler, Ratekau; Wolf-Dieter Schmidt, Lübeck, both of Fed. Rep. of Germany

[73] Assignee: Drägerwerk Aktiengesellschaft, Lübeck, Fed. Rep. of Germany

[21] Appl. No.: 258,474

[22] Filed: Oct. 17, 1988

Related U.S. Application Data

[62] Division of Ser. No. 195,305, May 18, 1988, Pat. No. 4,801,385.

[51] Int. Cl.[4] ............................................. B01D 13/01
[52] U.S. Cl. ............................. 210/321.8; 210/321.89
[58] Field of Search ............... 210/634, 637, 640, 641, 210/649–654, 257.2, 321.88, 321.89, 321.71, 321.78, 321.79, 500.23, 321.8; 55/158, 16; 261/104, DIG. 65; 128/204.13, 204.17

[56] References Cited

U.S. PATENT DOCUMENTS

| 4,146,597 | 3/1979 | Eckstein et al. | 261/104 |
| 4,318,398 | 3/1982 | Oetjen et al. | 128/204.13 |
| 4,355,636 | 10/1982 | Oetjen et al. | 128/204.13 |
| 4,381,267 | 4/1983 | Jackson | 261/104 |

Primary Examiner—Frank Sever
Attorney, Agent, or Firm—Walter Ottesen

[57] ABSTRACT

A substance exchange system especially for humidifying gases has at least one bundle of hollow fibers wherein a first flow space surrounds the outside of the hollow fibers and a second flow space is formed by the inner spaces of the hollow fibers with the exchange between the flow spaces being dependent on the exchange characteristic values of the hollow fibers. This substance exchange system is improved with respect to a more flexible determination of exchange quantities which are mutually independent. According to the invention, at least two sub-regions having hollow fibers of different exchange characteristic values are provided.

10 Claims, 2 Drawing Sheets

SYSTEM FOR EXCHANGING A SUBSTANCE BETWEEN FLUIDS

FIELD OF THE INVENTION

This is a division of application ser. No. 195,305 filed May 18, 1988 now U.S. Pat. No. 4,801,385.

The invention relates to an exchange system for exchanging a substance between fluids such as for the humidification of gases. The exchange system has at least one bundle of hollow fibers for which a first flow space surrounds the outer surfaces of the hollow fibers and a second flow space is formed by the inner spaces of the hollow fibers with the exchange between the flow spaces being dependent upon the exchange characteristic values of the hollow fibers. The invention also relates to a method for operating a system of the invention.

BACKGROUND OF THE INVENTION

Exchange systems wherein at least one bundle of hollow fibers is utilized are used in various ways for the exchange of a substance between two fluids. The one fluid flows on the outer side of the hollow fibers in a first flow space whereas the other fluid is conducted in the second flow space defined by the inner spaces of the hollow fibers. In actual use, so-called hollow-fiber modules are mostly used with each module having a housing in which the hollow fibers extend and wherein the first flow space is formed between the inner wall of the housing and the outer surfaces of the hollow fibers. A substance exchange system in the sense of this invention can comprise one or several of such hollow-fiber modules. Several modules form a system when they are connected with each other so that they together serve a specific substance exchange purpose.

Hollow fiber substance exchange systems are utilized for various purposes especially in the medical area such as for dialysis equipment or hemofiltration equipment. A further area of application is for the humidification of air which can, for example, be used in connection with apparatus for artificial respiration. Such breathing-air humidifiers are disclosed in U.S. Pat. Nos. 4,146,597 and 4,318,398 as well as in European Patent Publication No. 0,009,543 which corresponds to U.S. patent application Ser. No. 923,905 filed on July 12, 1978 and U.S. patent application Ser. No. 046,943 filed on June 8, 1979. The invention is especially directed to such substance exchange systems for the humidification of gases such as breathing air.

The walls of hollow fibers preferably comprise semipermeable membranes which make possible a selective transfer of substances from one fluid into the other. For the humidification of breathing air, water flows through the first flow space. The breathing air is conducted through the second flow space, that is, the breathing air is conducted through the interior of the hollow fibers. The water is usually heated. The hollow fibers are permeable for water molecules so that the breathing air flowing in their inner space is humidified. The degree of humidification is dependent upon the material characteristics of the hollow fibers and is especially dependent upon the magnitude of the pores of the fibers and upon the dimensions (wall thickness and diameter) of the fibers in the module. These influencing quantities are here grouped together and identified as the substance exchange characteristic values of the hollow fibers. In addition, the degree of humidification of the breathing air is also dependent upon the temperature of the water flowing through the first flow space because its vapor pressure increases with increasing temperature.

In the area of the humidification of breathing air, it is intended that the breathing air be warmed to a temperature which is favorable for the patient. The degree of heating is dependent upon the heat conductive capacity of the hollow fibers and upon the dimensions (wall thickness and diameter) thereof. These can be collectively referred to as the heat exchange characteristic values. In addition, the heating of the breathing air is dependent upon the temperature of the water.

If the temperature of the water flowing through the first flow space is changed, then the quantity of heat exchanged also changes as does the exchanged quantity of water in correspondence to the particular exchange characteristic values. As a consequence of the foregoing, it is not possible to vary the moisture content and the temperature of the breathing air independently of each other. This, however, would be desirable because from a medical point of view, different proportions with respect to moisture and temperature of the breathing air should be possible for various patients and for various application purposes. The moisture and the temperature of the breathing air should be changeable during the operation of the system. Similar problems exist in other areas wherein the substance exchange module can be utilized and wherein an undesired coupling of the exchange of different substances and/or energies exists because of the given exchange characteristic values.

SUMMARY OF THE INVENTION

In view of the foregoing, it is an object of the invention to provide a substance exchange system which provides a greater flexibility with respect to the exchange of substances and energy as has heretofore been achieved.

The substance exchange system of the invention is especially for the humidification of gases and has at least one hollow fiber bundle for which a first flow space surrounds the outer surfaces of the hollow fibers and a second flow space is formed by the inner spaces of the hollow fibers with the exchange between the flow spaces being dependent upon the exchange characteristic values of the hollow fibers. According to a feature of the invention, at least two sub-regions are provided having hollow fibers of different exchange characteristic values.

For example, hollow fibers having a high substance exchange capacity and especially a very good efficiency for the humidification of air can be combined in one system with other hollow fibers which are substantially or completely impermeable to water; however, they have special characteristics with respect to their heat conductivity. In this way, overall exchange characteristics are provided which are not obtainable with the system having only one hollow fiber type.

The substance exchange system according to the invention can, in the simplest case, comprise a plurality of substance exchange modules which contain hollow fibers of different exchange characteristic values. The spaces surrounding the outer sides of the hollow fibers are connected with each other by lines and a first fluid such as heated water flows therethrough so that these spaces conjointly define a first flow space. A second fluid such as air passes through the inner spaces of the hollow fibers of all substance exchange modules and the inner spaces of the hollow fibers conjointly define the second flow space. The exchange modules can be connected in series or in parallel in accordance with the particular application.

Pursuant to a preferred embodiment, a flow switchover between sub-regions of the hollow fibers by means of a control member is possible. A control member such as a selector valve can be provided in the conduit system for the situation where the substance exchange system comprises a plurality of substance exchange modules. The breathing air is distributed in a breathing-air humidification system to different substance exchange modules in accordance with the position of the control member and is humidified and heated in accordance with the exchange characteristic values of the modules. The position can be changed also during operation.

Distribution of the flows to the different sub-regions of the second flow space with the aid of the control member is preferably so configured that the quantity of fluid flowing through one sub-region reduces whereas the fluid quantity flowing through the other sub-region increases. Preferably, the total resistance of the flow through the second flow space remains constant.

BRIEF DESCRIPTION OF THE DRAWINGS

The invention will now be explained with reference to the drawings wherein.

DESCRIPTION OF THE PREFERRED EMBODIMENTS OF THE INVENTION

Figure 1:
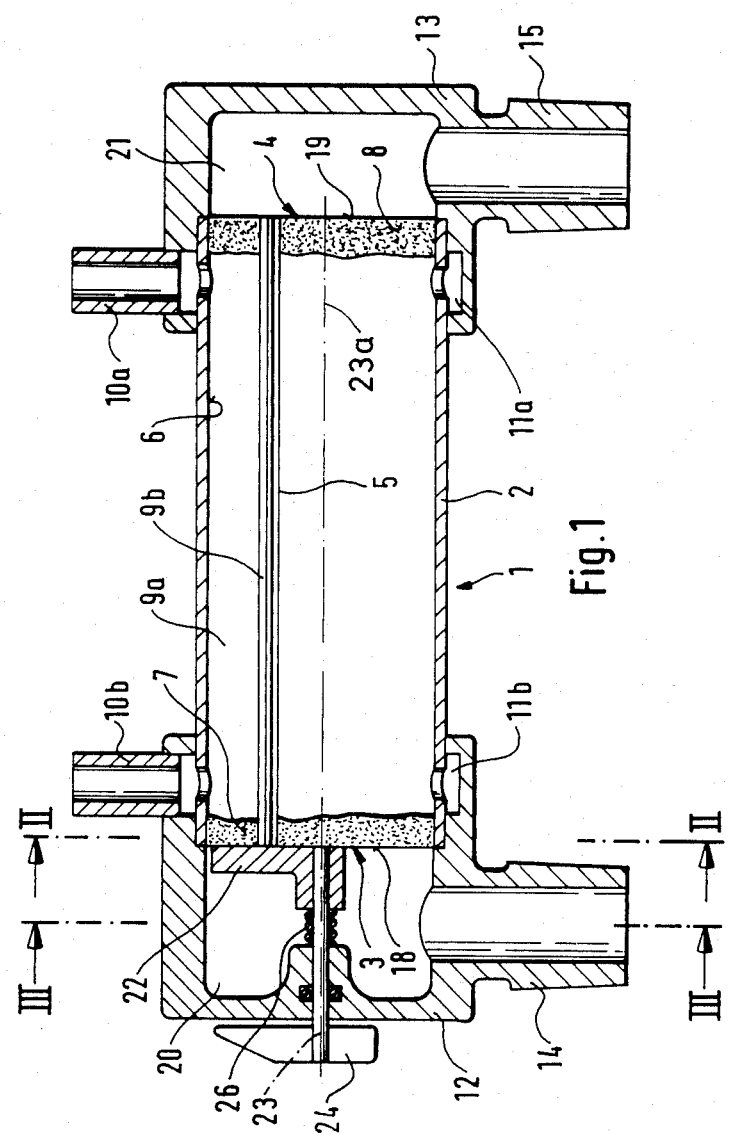
FIG. 1 is an elevation view, in longitudinal section, of a substance exchange module for humidifying breathing air.

The drawings show a substance exchange module 1 wherein different sub-regions having hollow fibers of different exchange characteristic values are arranged in a single housing 2. The housing 2 has a cylindrical shape and has two circular-shaped openings 3 and 4. A plurality of hollow fibers extend in the housing parallel to the axis 23a and are shown schematically in FIG. 1. The ends of the hollow fibers 5 are connected with each other and with the inner wall 6 of the housing in a liquid-tight manner in the region of the housing openings 3 and 4. This is realized by means of a casting mass (7, 8) in the illustrated embodiment.

The first flow space 9a surrounds the outer sides of the hollow fibers 5 and is limited outwardly by the housing 2. The first flow space 9a can be connected via two connecting stubs (10a, 10b) and two annular channels (11a, 11b) to a circulation loop for a first fluid.

End pieces (12, 13) are placed in a seal-tight manner on the openings (3, 4) of the housing 2. The end pieces (12, 13) are provided with respective connecting stubs (14, 15). The second space 9b defined by the inner spaces of the hollow fibers can be connected to a circulation loop for a second fluid via the connecting stubs (14, 15) and the end pieces (12, 13).

In the case of the breathing-air humidifier shown, the first fluid is heated water and the second fluid is breathing air. The hollow fibers are shown schematically as mentioned above and are preferably made of polysulfone and have an inner diameter of approximately 1 to 3 mm and a wall thickness of 0.05 mm to 0.2 mm. The hollow-fiber module generally contains several hundred hollow fibers. Insofar as the breathing-air humidifier has been described thus far with respect to FIG. 1, it is similar to that shown in European Patent No. 0,009,543 and it can be produced and operated in the manner described therein. Features of the exchange system of the invention are also shown in FIG. 1 and will be described below in conjunction with FIGS. 2 to 4.

Figure 2:
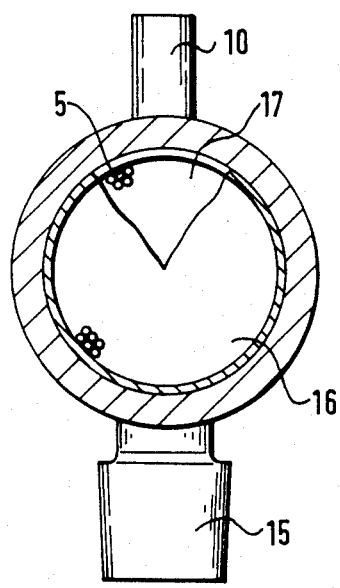
FIG. 2 is a cross section taken along line II—II of FIG. 1.

The hollow fibers in the housing 2 are not all the same and, instead, are subdivided into two sub-regions 16 and 17 in the embodiment disclosed with the hollow fibers of the sub-regions differing from one another with respect to their exchange characteristic values. As shown in FIG. 2, the sub-regions (16, 17) are each arranged as having the shape of the sector of a circle when viewed in the cross section of the housing 2.

The ends of the hollow fibers 5 together with the protruding casting mass (7, 8) are evenly cut during the manufacture of the module after casting. In this way, an inlet plane (18, 19) is formed at each opening (3, 4) of the housing 2 in which the inner spaces of the hollow fibers 5 open into the inner spaces (20, 21) of the respective end pieces (12, 13).

On one of the inlet planes 18, a blocking member 22 is pivotable with a shaft 23 coaxial to the housing 2. The blocking member 22 has essentially the shape of the sector of a circle. The blocking member 22 can be actuated by means of an adjusting button 24 attached to the shaft 23. The control member 22 is displaceable with the shaft 23 in the axial direction and is pressed against the inlet plane 18 by means of a compression spring 26.

During operation, the breathing air is supplied via the connecting stub 14 and flows through the second flow space 9b defined by the inner spaces of the hollow fibers and reaches the patient via the connecting stub 15. At the same time, water of a specific temperature circulates through the first flow space 9a and is supplied via connecting stub 10a and is directed away via connecting stub 10b. A portion of the inlet openings of the hollow fibers in the inlet plane 18 are closed by means of the blocking member 22.

Figure 3:
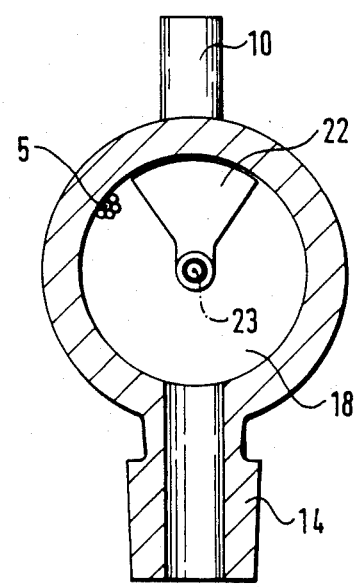
FIG. 3 is a cross section taken along line III—III of FIG. 1.

In the illustrated embodiment, the sub-region of the hollow fiber inlet openings blocked by the blocking member 22 is approximately as large as the sub-region 17 of the hollow fibers so that the blocking member 22 virtually completely blocks the sub-region 17 of the hollow fibers when the blocking member 22 is in the position shown in FIG. 3. The exchange then takes place only via the sub-region 16 of the hollow fibers.

As a consequence of the above, the quantity of heat and moisture transferred from the water to the breathing air corresponds to the exchange characteristic values of the hollow fibers in the sub-region 16. The more the blocking member 23 is pivoted out of the position shown in FIG. 3, the more are the openings of the hollow fibers in the sub-region 17 exposed while at the same a portion of the entrance openings of the hollow fibers in the sub-region 16 are closed. In this way, the characteristics of the module as a whole are changed in the direction toward the exchange characteristic values of the hollow fibers in the sub-region 17.

The foregoing will now be explained in greater detail with respect to a specific example.

Figure 4:
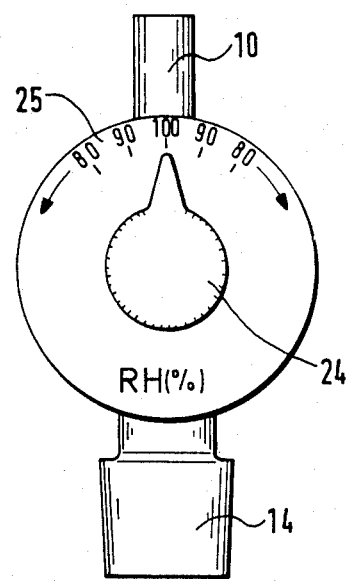
FIG. 4 is a plan view of the end face of the module of FIG. 1.

The sub-region 16 contains hollow fibers which have a heat-exchange characteristic value at a specific water temperature $T_l$ which assures a desired heating of the breathing air to a temperature $T_2$ and at the same time, at the same water temperature, leads to a water-saturation of the breathing air, that is, to a relative air humidity of 100%. The sub-region 17 contains hollow fibers which, with respect to their heat-exchange characteristic value, are not different from those in sub-region 16, but are impermeable to water. In a module of this kind, an air humidity of 100% is obtained with a simultaneous heating of the breathing air to $T_2$ for the center position shown in FIG. 3. By displacing the position of button 24 and thereby the blocking member 22, a portion of the water-permeable hollow fibers are blocked while at the same time a corresponding portion of the water-impermeable hollow fibers are exposed. In this way, the water transmission in the entire module becomes less and the reduced humidification of air is obtained at a temperature $T_2$ of the breathing air which remains constant. The end piece 12 can be provided with a scale 25 on the outside thereof as shown in FIG. 4.

In the embodiment described above, it is therefore possible to alter the total exchange in the module with reference to one exchange quantity (degree of humidification) without having to simultaneously alter a second exchange quantity (heat transfer) in a manner which perforce results from the exchange characteristic values of the hollow fibers utilized. With respect to the foregoing, it is noted that the second exchange quantity is essential for the function of the module. It is especially possible to hold the heat transfer constant and simultaneously vary the humidification. This change can be undertaken during the operation of the air humidifier.

Insofar as the flow resistance per unit surface of the inlet plane 18 is the same in the sub-regions 16 and 17, the flow resistance of the breathing air is independent of the position of the blocking member 22.

In several applications, it is furthermore desirable that the breathing air temperature as well as its humidification are selectable fully independently of each other within specific limits. For this purpose, at least three sub-regions of hollow fibers having different exchange characteristic values are required. The operation of such a module can best be explained with respect to a further example.

If an adjustability of the temperature between 35° and 40° C. is desired and the humidification of the breathing air between 80 and 100% relative humidity is to be made possible, then three different sub-regions A, B, C of hollow fibers are utilized with each taken separately leading to the following results with respect to temperature and humidity of the breathing air at a predetermined water temperature $T_o$ (that is, when 100% of the breathing air flows through a particular sub-region):

| A: 40° C., | 100% rh (relative humidity) |
|---|---|
| B: 40° C., | 0% rh |
| C: 18° C., | 0% rh |

On this basis, the corner points of the desired range can be realized wherein the breathing air is permitted to flow through the individual sub-regions of the hollow fibers in the percentages listed in the table below:

| 100% A | 40° C., | 100% rh |
|---|---|---|
| 25.6% C + 74.4% A | 35° C., | 100% rh |
| 21.6% B + 78.4% A | 40° C., | 80% rh |
| 58.6% A + 18.6% B + 22.8% C | 35° C., | 80% rh |

The same result is also obtainable with other values of three sub-regions of the hollow fibers which can be determined empirically or with the aid of a Mollier h—x diagram for humid air.

The function of the entire system is essentially independent of the direction of flow of the fluids shown in the example.

It is understood that the foregoing description is that of the preferred embodiments of the invention and that various changes and modifications may be made thereto without departing from the spirit and scope of the invention as defined in the appended claims.

What is claimed is:

1. An exchange system for exchanging a substance between fluids, the exchange system comprising:
   a housing;
   a bundle of hollow fibers mounted in said housing;
   said housing and the outer sides of said hollow fibers conjointly defining a first flow space for conducting a first fluid therethrough;
   said hollow fibers having respective interiors conjointly defining a second flow space for conducting a second fluid therethrough;
   a first set of said fibers defining a first exchange characteristic value and a second set of said fibers defining a second exchange characteristic value with the exchange of the substance between said flow spaces being dependent upon said exchange characteristic values; and,
   means for selectively dividing the flow of said second fluid between said sets of fibers for adjusting the exchange of the substance between said fluids.

2. The exchange system of claim 1, comprising:
   liquid supply means communicating with said first flow space for supplying a liquid thereto; and,
   gas supply means communicating with said second flow space for supplying a gas thereto.

3. The exchange system of claim 2, wherein the exchange system is for humidifying air and said liquid being water and said gas being air.

4. The exchange system of claim 2, the hollow fibers of each of said first and second sets being dimensioned and configured so as to cause said first and second exchange characteristic values to differ with respect to permeability and heat conductance of the fibers.

5. The exchange system of claim 2, said hollow fibers being further grouped into a third set of fibers dimensioned and configured to have a third exchange characteristic value.

6. The exchange system of claim 1, comprising control means for switching the flow through the hollow fibers of said first and second sets.

7. The exchange system of claim 6, said control means being mounted so as to be switchable from a first position to a second position so as to cause the flow through said first set of hollow fibers to decrease while the flow through said second set of hollow fibers increases.

8. The exchange system of claim 7, said control means being configured so as to cause the resistance to flow through said second flow space to remain approximately constant when said control means is switched between said first and second positions.

9. The exchange system of claim 6, said housing having an inner wall surface and first and second end regions; each of said fibers having first and second end portions at corresponding ones of said end regions; said housing including first joining means for joining the first end portions of said fibers to each other and to said inner wall surface in said first end region of said housing and second joining means for joining the second end portions of said fibers to each other and to said inner wall surface at said second end region of said housing; said joining means and the first end portions of said fibers conjointly defining an entry plane at which said second flow space communicates with said first end region; said system further including second fluid supply means for supplying said second fluid to said first end region; and, said control means including a blocking member mounted so as to be movable across said entry plane to block the passage of said second fluid through selected ones of said fibers.

10. The exchange system of claim 9, said fibers being arranged one next to the other to conjointly define a cylinder thereby causing the end faces of said first end portions to define said entry plane as a circle; the fibers of said first and second sets being arranged within said cylinder so as to define respective sectors of said circle; and, said control means including an actuating shaft rotatably mounted in said housing so as to define a longitudinal axis extending through the center of said circle in a direction perpendicular to said entry plane; and, said blocking member being mounted on said shaft for rotation therewith and having the shape of a sector of a circle.

* * * * *

UNITED STATES PATENT AND TRADEMARK OFFICE
CERTIFICATE OF CORRECTION

PATENT NO. : 4,859,331
DATED : August 22, 1989
INVENTOR(S) : Jürgen Sachtler and Wolf-Dieter Schmidt It is certified that error appears in the above-identified patent and that said Letters Patent is hereby corrected as shown below:

In column 4, line 60: insert -- time -- between "same" and "a".

In column 5, line 1: delete "temperature $T_l$" and substitute -- temperature $T_1$ -- therefor.

In column 6, line 1: delete "+ 22,8% C" and substitute -- + 22.8% C -- therefor.

Signed and Sealed this

Thirty-first Day of July, 1990

*Attest:*

HARRY F. MANBECK, JR.

*Attesting Officer*     *Commissioner of Patents and Trademarks*